United States Patent [19]
Lawson

[11] 3,936,355
[45] Feb. 3, 1976

[54] MICROORGANISM GROWTH MEDIA AND THE STABILIZATION THEREOF

[75] Inventor: John W. Lawson, Kansas City, Mo.

[73] Assignee: The Regents of the University of California, Berkeley, Calif.

[22] Filed: Nov. 12, 1973

[21] Appl. No.: 415,013

[52] U.S. Cl. .................................................. 195/100
[51] Int. Cl.² ........................................... C12K 1/10
[58] Field of Search ..................... 195/100, 101, 102

[56] References Cited
UNITED STATES PATENTS

| | | | |
|---|---|---|---|
| 3,669,846 | 6/1972 | Thuillier | 195/96 |
| 3,671,400 | 6/1972 | Cekoric et al. | 195/100 |
| 3,816,261 | 6/1974 | Torney | 195/100 |

OTHER PUBLICATIONS

Tissue Culture Reagents, Hyland Laboratories, p. 14, Oct. 1963.

Primary Examiner—A. Louis Monacell
Assistant Examiner—C. A. Fan
Attorney, Agent, or Firm—Phillips, Moore, Weissenberger Lempio & Strabala

[57] ABSTRACT

Media for supporting the growth of certain types of microorganisims, especially Neisseria gonorrhoeae and Neisseria meningitidis, are described. These media, when supplemented with polyvinylpyrrolidone (PVP), albumin and penicillin induce microorganism transformation to the wall-defective or "L-form." The PVP is necessarily "detoxified" for use in the L-form inducing media.

4 Claims, No Drawings

MICROORGANISM GROWTH MEDIA AND THE STABILIZATION THEREOF

BACKGROUND OF THE INVENTION

It has been postulated that penicillin failures in the treatment of gonorrhea may be the result of conversion of normal cell forms of Neisseria gonorrhoeae to the wall-defective or L-form. The L-form of the gonococcus can continue to exist and reproduce in the presence of penicillin and this may account for chronic infection despite antibiotic therapy. Similar conversions of normal cells to wall-defective forms has been noted in the case of Neisseria meningitidis.

In order to elucidate the role of wall-defective gonococi, it is necessary to secure their in vitro conversion and growth. However, success in this area has not been easy to achieve, although some success has been reported by Roberts in the Journal of Bacteriology, vol. 92, pages 1609–1614 (1966) on a sucrose stabilized medium. Lawson and Douglas have reported in the Canadian Journal of Microbiology, September 1973, (abstracted at 1972 Annual Meeting of the American Society for Microbiology) that PVP stabilized media comprising brain heart infusion broth, agar, horse serum, and penicillin is useful in inducing conversion to the L-form. Also of interest in U.S. Pat. No. 3,669,846, issued June 13, 1972 in class 195/96 for "Process for Obtaining and Preserving Stable Bacterial Variants"; as well as U.S. Pat. No. 3,687,816, issued Aug. 29, 1972 in class 195/100 for "Bacterial Growth Media"; U.S. Pat. No. 3,098,016, issued July 16, 1963 in class 195/102 for "Process for Preparing Sterile Vials Containing Culture Media and a Carbon Dioxide Atmosphere"; U.S. Pat. No. 3,477,914, issued Nov. 11, 1969 in class 195/96 for "Treating Method of Streptococcus Hemolytics and the Preparation Containing the Said Microorganism"; and U.S. Pat. No. 3,527,712, issued Sept. 8, 1970 in class 252/316 for "Dried Agarose Gel, Method of Preparation Thereof, and Production of Aqueous Agarose Gel".

BRIEF SUMMARY OF THE INVENTION

Defined media have now been devised that are suitable for converting cocci to the L-form and further propagating the L-form organisms.

More specifically a medium has been devised that is eminently suitable for growing strains of N. gonorrhoeae or N. meningitidis either in broth or on agar. This medium comprises a standard virology tissue culture medium known as "Medium 199" in combination with cysteine, the sodium salt of glycerophsophate, KCl, NaCl, NH$_4$Cl, MgSO$_4$.hydrate and glucose.

Medium 199 is a standardized tissue culture medium available from Grand Island Biological Co., Grand Island, N.Y., and comprises an extensive list of amino acids, salts, and other nutrients. This medium is "standardized" and is well known to microbiologists. It is available on an "off-the-shelf" basis.

Specifically, standardized Medium 199 has the following composition, with amounts stated per liter of the Medium:

| | |
|---|---|
| L-Arginine | 70 mg |
| L-Histidine | 20 mg |
| L-Lysine monohydrochloride | 70 mg |
| DL-tryptophane | 20 mg |
| DL-Phenylalanine | 50 mg |
| DL-Methionine | 30 mg |
| DL-Serine | 50 mg |
| DL-Threonine | 60 mg |
| DL-Leucine | 120 mg |
| DL-Isoleucine | 40 mg |
| DL-Valine | 50 mg |
| DL-Glutamic acid monohydrate | 150 mg |
| DL-Aspartic acid | 60 mg |
| DL-α-Alanine | 50 mg |
| L-Proline | 40 mg |
| L-Hydroxyproline | 10 mg |
| Glycine (Aminoacetic acid) | 50 mg |
| L-Glutamine | 100 mg |
| Sodium acetate trihydrate | 50 mg |
| L-Cystine | 20 mg |
| L-Tryosine | 40 mg |
| L-Cysteine hydrochloride | 0.1 mg |
| Adenine | 10 mg |
| Guanine | 0.3 mg |
| Xanthine | 0.3 mg |
| Hypoxanthine | 0.3 mg |
| Uracil | 0.3 mg |
| Thymine (5-methyl uracil) | 0.3 mg |
| Disodium α-tocopherol phosphate | 0.01 mg |
| Thiamine | 0.01 mg |
| Pyridoxine hydrochloride | 0.025 mg |
| Riboflavin | 0.01 mg |
| Pyridoxal hydrochloride | 0.025 mg |
| Niacin | 0.025 mg |
| Calcium pantothenate | 0.01 mg |
| i-Inositol | 0.05 mg |
| Ascorbic acid | 0.05 mg |
| Folic acid | 0.01 mg |
| p-Aminobenzoic acid | 0.05 mg |
| Ferric Nitrate | 0.1 mg |
| Biotin | 0.01 mg |
| Menadione | 0.01 mg |
| Glutathione | 0.05 mg |
| Vitamin A | 0.1 mg |
| Calciferol | 0.1 mg |
| Adenosine triphosphate (disodium salt) | 1.0 mg |
| Tween 80 (Atlas Powder Co.) | 5.0 mg |
| Cholesterol | 0.2 mg |
| Niacinamide | 0.025 mg |
| Adenylic acid | 0.2 mg |
| Desoxyribose | 0.5 mg |
| D-Ribose | 0.5 mg |
| Choline chloride | 0.5 mg |
| NaCl | 8.0 mg |
| KCl | 0.4 mg |
| MgSO$_4$.7H$_2$O | 0.2 mg |
| Na$_2$HPO$_4$.7H$_2$O | 0.09 mg |
| KH$_2$PO$_4$ | 0.06 mg |
| Glucose | 1.0 mg |
| Phenol Red | 0.02 mg |
| CaCl$_2$ | 0.14 mg |
| NaHCO$_3$ | 0.35 mg |

If the medium for growing cocci is modified, appreciable conversion of the cocci to the wall defective L-form takes place and this medium is also suitable for propagating the L-form. The medium is modified by the addition of albumin, detoxified, PVP, and penicillin thereto.

L-form propagation is also advantageously carried out on a solid medium, and in this instance, the medium is solidified with agarose.

It is also extremely important to utilize detoxified PVP to secure the highest induction of the L-form and good propagation thereof. The method for producing detoxified PVP is fully explained hereinafter.

It is therefore an object of the invention to provide a medium that is useful for propagation of cocci.

It is another object of the invention to provide media, in both liquid and solid form, suitable for effecting induction of the L-form of cocci, especially Neisseria gonorrhoeae and Neisseria meningitidis.

It is another object of the invention to provide detoxified polyvinylpyrrolidone useful in stabilizing L-form induction and growth media. Other objects and advantages of the invention will become apparent from the following specification and claims appended hereto.

DETAILED DESCRIPTION OF THE INVENTION

The present invention provides a synthetic medium suitable for the growth of cocci, e.g., N. gonorrhoeae. The same medium may be utilized in either the broth or solidified form. Normally the liquid or broth medium is solidified through the addition of agar thereto. Transformation of the normal cocci into the L-form is achieved by growing the cocci in the synthetic medium to which detoxified PVP and albumin as well as penicillin has ben added. Normally induction of the L-form is carried out on the solid synthetic medium but it is contemplated that the same may also be conducted in the liquid medium.

The liquid medium for growth of the normal gonococci principally comprises a standard tissue culture medium known as Medium 199. This medium is a standardized composition of amino acids, salts and the like obtainable from the Grand Island Biological Company of Grand Island, New York. To the Medium 199 base is added cysteine, the sodium salt of glycerophosphate, potassium chloride, sodium chloride, ammonium chloride, hydrated magnesium sulfate and glucose. A preferred synthetic growth medium comprises, per liter, about 50 mls of Medium 199 at 10x dilution, about 0.012 grams of L-cysteine hydrochloride, about 2.5 grams of sodium glycerophosphate, about 0.09 grams potassium chloride, about 6.0 grams sodium chloride, about 1.25 grams ammonium chloride, about 0.6 grams magnesium sulfate septahydrate and about 5 grams of glucose. The pH is adjusted to about 7.0 by the addition of 2N-sodium hydroxide to the broth. Triple distilled water is utilized in all formulations.

Standard procedures in utilizing pharmaceutical grade components and biologically sterilized equipment are followed.

When growth is to be carried out in the liquid medium the desired strains of cocci are inoculated into the broth. The broth is incubated at 37°C and the cultures are sub-cultured daily. An initial inoculum size of about 10% is followed. However, once the organisims are adapted to the synthetic medium the inoculum size can be decreased in a stepwise fashion from the 10% down to about 1%.

For induction to the L-form, solid medium is most suitable. The solid medium is prepared by the addition of about 15 grams of agarose added to the above-noted liquid medium per liter. The solidified medium also has detoxified PVP and albumin incorporated therein. The solid medium is prepared in the form of plates and penicillin is spread over the surface thereof prior to inoculation with cocci cultures obtained from the liquid broth.

Conversion of the cocci to the L-form and subsequent propogation thereof is carried out by incubating the plates at about 37°C in a sealed chamber. For a high yield conversion to the L-form it has also been found necessary to flush the sealed chamber with a gaseous mixture of $CO_2$ in air. $CO_2$ should be present in an amount of at least 5%, but preferably 10% $CO_2$ should be maintained in the atmosphere over the plates. Under the conditions stated above colonies of the L-form cocci appear on the solid medium within 18–24 hours.

Incubation for 18–30 hours results in the growth of visible colonies of cocci. Sampling of these colonies will reveal that conversion to the L-form has taken place in good yield. The L-form may be harvested and thereafter propogated by inoculating the same onto additional plates of the same medium.

In L-form induction on solid medium excellent induction and growth occurs in the presence of about 2% albumin. Bovine albumin such as fraction V from bovine plasma avaiable from Reheis Chemical Company, Chicago, Illinois is particulary suitable for this purpose. Similarly agarose (obtainable from Bio-Rad Laboratories, Richmond, California) is preferred for solidifying the liquid medium. Induction and growth of L-form gonococci proceeds well on medium solidified with agarose.

It is especially important to provide osmotic stabilization of the medium by the addition of detoxified PVP. Detoxification is necessary to insure adequate conversion and propogation of the L-form. Detoxification is achieved as follows:

Pharmaceutical grade PVP having an average molecular weight of approximately 40,000 (available from Sigma Chemical Company, St. Louis, Missouri) is dialyzed at 4°C against two ion exchange resins (carboxymethyl cellulose and DEAE dextran) in sequence. Subsequent to the dialysis against the ion exchange resins, the PVP is dialyzed for a period of 48 hours against deionized distilled water. The water is frequently changed during the dialysis period. The retentate is then concentrated by freeze drying.

The detoxified PVP is rehydrated and mixed into the growth medium in an amount of approximately 8% by weight. Prior to cocci inoculation, penicillin in an amount of about 20 units per milliliter is applied to the growth medium on which conversion to the L-form is desired.

EXAMPLE

Cultures of Neisseria gonorrhoeae, strains 474, a genital isolate, 448, a throat isolate, and GC3, a fresh clinical isolate were obtained from the Neisseria Repository, Naval Medical Research Unit No.1, University of California, Berkeley, California.

All three strains were initially grown in MuellerHinton broth, which is a medium known to support N. gonorrhoeae growth. After establishment, the strains were inoculated into a broth comprising:

| | |
|---|---|
| Medium 199-10X | 50 ml/l |
| l-cysteine-HCl | 0.012 g/l |
| Na-glycerophosphate | 2.5 g/l |
| KCl | 0.09 g/l |
| NaCl | 6.0 g/l |
| $NH_4Cl$ | 1.25 g/l |
| $MgSO_4.7H_2O$ | 0.6 g/l |
| Glucose | 5 g/l |

The broth cultures were subcultured daily and incubated at 37°C. Once the strains were adapted to the medium, the inoculum size was decreased in a stepwise fashion from 10% to 1%.

The strains, after adaptation to the synthetic broth medium, were transferred for induction to the L-form, by sampling 12 hour cultures. These cultures were plated on solid media prepared by mixing the broth composition stated above with about 2% albumin, and about 8% detoxified PVP. Solidification was achieved by addition of about 2% agarose, while about 20 units/ml. of penicillin G was also added.

The solid medium plates were then incubated at 37°C in a sealed chamber flushed with an atmosphere of 10%

$CO_2$ in air. Incubation was continued for 10–14 days in the $CO_2$ enriched atmosphere.

The number of parental gonococci was determined by plating samples from culture dilutions made in the broth medium on both solid medium without the addition of penicillin and on Mueller-Hinton blood agar plates.

Colonies of L-form strains 474 and 448 became visible on the solid medium plates within 18–24 hours. The growth of L-form strain GC3 tended to be slower, but colonies were usually visible after 30 hours.

The growth and induction of the L-form for the strains is shown in the Table below:

| Strain | Parental Viable Counts (CFU/ml)[b] MH-BAP[a] | L-Medium without penicillin | L-Form viable count (CFU/ml)[b] L-Medium with penicillin | % Induction to the L-Form |
|---|---|---|---|---|
| 474 | $2.3 \times 10^8$ | $2.7 \times 10^8$ | $7.9 \times 10^5$ | 0.3 |
| 448 | $2.8 \times 10^8$ | $2.6 \times 10^8$ | $9.8 \times 10^4$ | 0.04 |
| GC3 | $3.7 \times 10^8$ | $3.2 \times 10^8$ | $5.8 \times 10^4$ | 0.02 |

[a] = Mueller-Hinton blood agar plates
[b] = colony forming units/ml.

What is claimed is:

1. A medium for the induction of the wall defective forms of cocci, including the genus neisseria, comprising a standard virology tissue culture medium known as Medium 199, and added amounts of cysteine, glycerophosphate, alkali metal chloride salts, ammonium chloride salt, magnesium sulfate, glucose, detoxified polyvinylpyrrolidone albumin, and penicillin.

2. The medium of claim 1 solidified with agarose.

3. The medium of claim 1 wherein the components are present in the amounts of about 50 ml/l of the standard virology tissue culture, and added amounts of about 0.012 g/l of cysteine, about 2.5 g/l of glycerophosphate, about 0.09 g/l of KCl, about 6 g/l of NaCl, about 1.25 g/l of $NH_4Cl$, about 0.6 g/l of $MgSO_4 \cdot 7H_2O$, about 5 g/l of glucose, about 2% by weight albumin, about 8% by weight detoxified polyvinylpyrrolidone, and about 20 units/ml of penicillin.

4. The medium of claim 3 solidified with agarose.

* * * * *